(12) United States Patent
Miyaura et al.

(10) Patent No.: US 7,662,998 B2
(45) Date of Patent: Feb. 16, 2010

(54) METHOD FOR PRODUCING HEXAALKYLBORAZINE

(75) Inventors: Norio Miyaura, Sapporo (JP); Yasunori Yamamoto, Sapporo (JP); Yasutaka Nakatani, Higashiosaka (JP); Tetsuya Yamamoto, Nishinomiya (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/667,122

(22) PCT Filed: Oct. 28, 2005

(86) PCT No.: PCT/JP2005/020255

§ 371 (c)(1),
(2), (4) Date: Dec. 3, 2007

(87) PCT Pub. No.: WO2006/049229

PCT Pub. Date: May 11, 2006

(65) Prior Publication Data

US 2008/0188682 A1 Aug. 7, 2008

(30) Foreign Application Priority Data

Nov. 8, 2004 (JP) .............................. 2004-323830

(51) Int. Cl.
*C07F 5/02* (2006.01)
(52) U.S. Cl. ...................................................... 564/10
(58) Field of Classification Search ................... 564/10
See application file for complete search history.

(56) References Cited

U.S. PATENT DOCUMENTS

2002/0058142 A1 5/2002 Tsunoda et al.
2003/0100175 A1 5/2003 Nobutoki et al.

OTHER PUBLICATIONS

PCT/ISA/210 and PCT/IDS/237.

D.T. Haworth and L.F. Hohnstedt, J. Am. Chem. soc., vol. 82, p. 3860-3862 (1960).
Howard Steinberg and Robert J. Brotherton, "Organoboron Chemistry", John Wiley & sons, p. 244-249 , 2000.
V.A. Zamyatina and V.V. Korshak, "reaction of 1,3,5-trimethylcyclotriborazane with 1-hexene" Bull.Acad.Sci.USSRDiv. Chem. Sci, vol. 20, 1971, p. 1709-1711.
Paul J. Fazen and Larry G. Sneddon, Organometallics, 1994, 13, 2867-2877.

*Primary Examiner*—Jafar Parsa
(74) *Attorney, Agent, or Firm*—Buchanan Ingersoll & Rooney PC

(57) ABSTRACT

In synthesis of hexaalkylborazine represented by the chemical formula 2 from a borazine compound represented by the chemical formula 1, a borazine compound represented by the chemical formula 1 is reacted with an alkene compound, in the presence of a catalyst. Wherein $R^1$s may be the same or different and each $R^1$ represents an alkyl group; and each $R^2$ represents a hydrogen atom or an alkyl group, and at least one of $R^2$s represents a hydrogen atom; and $R^3$s may be the same or different and each $R^3$ represents an alkyl group.

[Chemical formula 1]

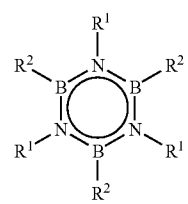

[Chemical formula 2]

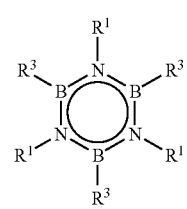

7 Claims, No Drawings

METHOD FOR PRODUCING HEXAALKYLBORAZINE

BACKGROUND OF THE INVENTION

1. Field of the Invention

The present invention relates to a method for producing hexaalkylborazine. Hexaalkylborazine is used to form, for example, an interlayer dielectric film for semiconductor, a barrier metal layer and an etching stopper layer.

2. Description of Related Art

With higher functionalization of information devices, design rule of LSI has been required to be finer year by year. In production of LSI with finer design rule, materials composing LSI should also have higher performance and fulfill function even on fine LSI.

For example, as for materials used for an interlayer dielectric film in LSI, high dielectric constant causes signal delay. In fine LSI, effects of the signal delay is particularly significant. Therefore, development of a new low dielectric material which can be used for an interlayer dielectric film has been needed. Also, it is necessary not only to have low dielectric constant but also superior characteristics such as humidity resistance, heat resistance, mechanical strength, etc. to be used as an interlayer dielectric film.

As a material to respond to these requirements, a compound having borazine ring backbone has been proposed (for example, see US Laid Open Patent No. 2002-58142). A compound having borazine ring backbone (borazine compound) has small molecular polarizability and thus a coated film formed provides low dielectric constant. Moreover, the coated film formed is superior in heat resistance.

As a borazine compound, various compounds have been proposed up to now (for example, see US Laid Open Patent No. 2003-100175). Hexaalkylborazine among borazine compounds, whose boron moiety and nitrogen moiety are both substituted with an alkyl group, has very superior characteristics as low dielectric material.

As a method for producing hexaalkylborazine, whose boron moiety and nitrogen moiety are substituted with an alkyl group, a method using a Grignard reaction is disclosed (for example, see D. T. HAWORTH and L. F. HOHNSTEDT, J. Am. Chem. Soc., 82, 3860 (1960), Howard Steinberg, Robert J. Brotherton, "ORGANOBORON CHEMISTRY", John Wiley & Sons, p 244-).

Also disclosed is a method for synthesizing a borazine compound whose hydrogen atom bonded to boron is substituted with an alkyl group, wherein borazine is reacted with an alkene compound in the presence of $RhH(CO)(PPh_3)_3$ (see Paul J. Fazen and Larry G. Sneddon, Organometallics, 1994, 13, 2867-2877). In this method, however, a starting compound is borazine not substituted with an alkyl group, and thus a compound synthesized is a borazine compound substituted with an alkyl group only at boron moiety.

BRIEF SUMMARY OF THE INVENTION

Investigation by the present inventors revealed that when a borazine compound is substituted with an alkyl group using a Grignard reagent, trialkylborane is included as a by-product in hexaalkylborazine synthesized. Trialkylborane is an unstable compound and has high ignition tendency. Trialkylborane has lower boiling point and more volatility than those of an objective compound, hexaalkylborazine, which may cause ignition by trialkylborane diffused in atmosphere. It is not certain now how much quantity of trialkylborane present in atmosphere induces natural ignition and also hexaalkylborazine produced by a conventional technology is not necessarily a hazardous compound. However, it is preferable for such a compound possibly not to present in view of safety of workers or facility.

In view of the above, an object of the present invention is to provide a method for suppressing by-production of trialkylborane in a production process of hexaalkylborazine bonded with an alkyl group at both a boron atom and a nitrogen atom.

The present invention provides: A method for producing hexaalkylborazine, wherein hexaalkylborazine represented by the chemical formula 2 is synthesized by a reaction of a borazine compound represented by the chemical formula 1 with an alkene compound, in the presence of a catalyst:

[Chemical formula 1]

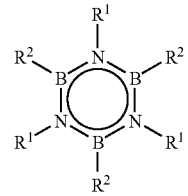

wherein $R^1$s may be the same or different and each $R^1$ represents an alkyl group; and each $R^2$ represents a hydrogen atom or an alkyl group, and at least one of $R^2$s represents a hydrogen atom:

[Chemical formula 2]

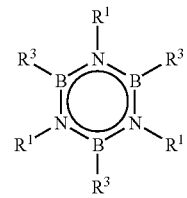

wherein $R^1$s and $R^3$s may be the same or different and each $R^1$ and $R^3$ represents an alkyl group.

By using a production method according to the present invention, by-production of trialkylborane can be suppressed in a production process. Therefore, highly safe hexaalkylborazine without including trialkylborane is provided.

DETAILED DESCRIPTION OF THE INVENTION

The present invention relates to a method for synthesizing hexaalkylborazine represented by the chemical formula 2 from a borazine compound represented by the chemical formula 1:

[Chemical formula 1]

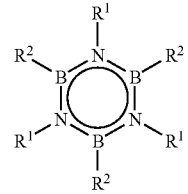

wherein $R^1$s may be the same or different and each $R^1$ represents an alkyl group; and each $R^2$ represents a hydrogen atom or an alkyl group, and at least one of $R^2$s represents a hydrogen atom:

[Chemical formula 2]

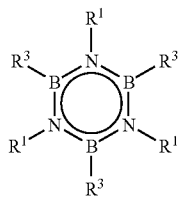

wherein $R^1$s and $R^3$s may be the same or different and each $R^1$ and $R^3$ represents an alkyl group.

Here, generation mechanism of trialkylborane in a production process of hexaalkylborazine is not certain, however, a Grignard reagent is considered to be one cause. If so, by adopting a production process without using a Grignard reagent, it is possible to suppress generation of trialkylborane. Based on this viewpoint, in the present invention, an alkyl substitution reaction of a borazine compound proceeds without using a Grignard reagent. Specifically, in the present invention, a borazine compound is reacted with an alkene compound to make an alkyl substitution reaction of a borazine compound. By adopting this production process, generation of trialkylborane is suppressed. In the present invention, "borazine" basically means borazine ($B_3N_3H_6$) without bonding of an alkyl group at both boron atom and nitrogen atom and "a borazine compound" means a borazine derivative wherein at least one of a boron atom and a nitrogen atom is substituted with a hydrogen atom.

Next, a production method of the present invention is explained in more detail.

First, a borazine compound represented by the chemical formula 1, used as raw material, is prepared.

[Chemical formula 1]

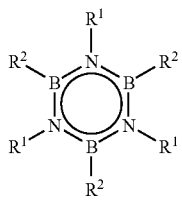

wherein each $R^1$ represents an alkyl group. $R^1$s may be the same or different. In consideration of yield or handling easiness of a synthesis reaction, $R^1$s are preferably the same alkyl groups. The alkyl group may be any of straight chain, branched or cyclic type. The number of carbon atoms of the alkyl group is not especially limited, however, preferably 1 to 8, more preferably 1 to 4 and further preferably 1. Specific examples of the alkyl group include such as methyl group, ethyl group, propyl group, isopropyl group, butyl group, isobutyl group, sec-butyl group, tert-butyl group, pentyl group, isopentyl group, neopentyl group, hexyl group, heptyl group, octyl group, nonyl group, decyl group, cyclopropyl group, cyclopentyl group and cyclohexyl group. Alkyl groups other than these may also be used.

Each $R^2$ represents a hydrogen atom or an alkyl group. $R^2$s may be the same or different, and at least one of three $R^2$s represents a hydrogen atom. The number of the hydrogen atom is not especially limited, however, one of $R^2$s may be a hydrogen atom, or two or all of three may be hydrogen atoms. In consideration of yield or handling easiness of a synthesis reaction of a compound used as raw material, it is preferable that all of $R^2$s are hydrogen atoms. The alkyl group may be any of straight chain, branched or cyclic type. The number of carbon atoms of the alkyl group is not especially limited. Specific examples of the alkyl group include such as methyl group, ethyl group, propyl group, isopropyl group, butyl group, isobutyl group, sec-butyl group, tert-butyl group, pentyl group, isopentyl group, neopentyl group, hexyl group, heptyl group, octyl group, nonyl group, decyl group, cyclopropyl group, cyclopentyl group and cyclohexyl group. Alkyl groups other than these may also be used.

Specific examples of a borazine compound represented by the chemical formula 1 include the following compounds, however, they are not limited to these:
N,N',N"-trimethylborazine, N,N',N"-triethylborazine,
N,N',N"-tri(n-propyl)borazine,
N,N',N"-tri(isopropyl)borazine,
N,N',N"-tri(n-butyl)borazine,
N,N',N"-tri(sec-butyl)borazine,
N,N',N"-tri(isobutyl)borazine,
N,N',N"-tri(tert-butyl)borazine,
N,N',N"-tri(1-methylbutyl)borazine,
N,N',N"-tri(2-methylbutyl)borazine,
N,N',N"-tri(neopentyl)borazine,
N,N',N"-tri(1,2-dimethylpropyl)borazine,
N,N',N"-tri(1-ethylpropyl)borazine,
N,N',N"-tri(n-hexyl)borazine,
N,N',N"-tricyclohexylborazine,
B-methylN,N',N"-trimethylborazine,
B-methyl-N,N',N"-triethylborazine,
B-methyl-N,N',N"-tri(n-propyl)borazine,
B-methyl-N,N',N"-tri(isopropyl)borazine,
B-methyl-N,N',N"-tri(n-butyl)borazine,
B-methyl-N,N',N"-tri(sec-butyl)borazine,
B-methyl-N,N',N"-tri(isobutyl)borazine,
B-methyl-N,N',N"-tri(tert-butyl)borazine,
B-methyl-N,N',N"-tri(1-methylbutyl)borazine,
B-methyl-N,N',N"-tri(2-methylbutyl)borazine,
B-methyl-N,N',N"-tri(neopentyl)borazine,
B-methyl-N,N',N"-tri(1,2-dimethylpropyl)borazine,
B-methyl-N,N',N"-tri(1-ethylpropyl)borazine,
B-methyl-N,N',N"-tri(n-hexyl)borazine,
B-methyl-N,N',N"-tricyclohexylborazine,
B-ethyl-N,N',N"-trimethylborazine,
B-ethyl-N,N',N"-triethylborazine,
B-ethyl-N,N',N"-tri(n-propyl)borazine,
B-ethyl-N,N',N"-tri(isopropyl)borazine,
B-ethyl-N,N',N"-tri(n-butyl)borazine,
B-ethyl-N,N',N"-tri(sec-butyl)borazine,
B-ethyl-N,N',N"-tri(iso-butyl)borazine,
B-ethyl-N,N',N"-tri(tert-butyl)borazine,
B-ethyl-N,N',N"-tri(1-methylbutyl)borazine,
B-ethyl-N,N',N"-tri(2-methylbutyl)borazine,
B-ethyl-N,N',N"-tri(neopentyl)borazine,
B-ethyl-N,N',N"-tri(1,2-dimethylpropyl)borazine,
B-ethyl-N,N',N"-tri(1-ethylpropyl)borazine,
B-ethyl-N,N',N"-tri(n-hexyl)borazine,
B-ethyl-N,N',N"-tricyclohexylborazine,
B,B'-dimethyl-N,N',N"-trimethylborazine,
B,B'-dimethyl-N,N',N"-triethylborazine,
B,B'-dimethyl-N,N',N"-tri(n-propyl)borazine,
B,B'-dimethyl-N,N',N"-tri(isopropyl)borazine,
B,B'-diethyl-N,N',N"-trimethylborazine, B,B'-diethylN,N',N"-triethylborazine,
B,B'-diethyl-N,N',N"-tri(n-propyl)borazine,
B,B'-diethyl-N,N',N"-tri(isopropyl)borazine,
B-methyl-B'-ethyl-N,N',N"-trimethylborazine,
B-methyl-B'-ethyl-N,N',N"-triethylborazine,
B-methyl-B'-ethyl-N,N',N"-tri(n-propyl)borazine,
B-methyl-B'-ethyl-N,N',N"-tri(isopropyl)borazine A method for getting a borazine compound is not especially limited. A borazine compound may be synthesized according to known methods or a borazine compound available on the market may be used.

An alkene compound to be reacted with a borazine compound represented by the chemical formula 1 is not especially limited as long as it has at least one double bond (C=C) between carbon atoms and can substitute hydrogen bonded to boron composing a borazine ring, with an alkyl group. Specific examples of the alkene compound include such as ethylene, propene, 1-butene, cis-2-butene, trans-2-butene, 2-methylpropene, 1-pentene, cis-2-pentene, trans-2-pentene, 2-methyl-1-butene, 3-methyl-1-butene, 2-methyl-2-butene, styrene, α-methylstyrene, 1,3-butadiene and 1,5-hexadiene.

Reaction mechanism of a borazine compound and an alkene compound is not clear; however, it is supposed to be as follows: An intermediate which has a bonding between a borazine compound and an alkene compound mediated by a catalyst, followed by direct bonding of a boron atom of a borazine compound and the alkene compound. However, the mechanism is only a speculation and the scope of the present invention is by no means limited to this mechanism.

In a reaction between a borazine compound and an alkene compound, a catalyst is used. The catalyst is not especially limited as long as it has a function to promote a reaction between a borazine compound and an alkene compound. As the catalyst, in view of catalytic activity, it is preferably a catalyst of a metal such as cobalt (Co), rhodium (Rh), ruthenium (Ru), iridium (Ir), nickel (Ni), paradium (Pd), platinum (Pt), titanium (Ti), zirconium (Zr) and lanthanoids (La, Sm, etc.). More specifically such as $RhCl(PPh_3)_3$, $RhCl(CO)(PPh_3)_2$, $RhH(CO)(PPh_3)_3$, $[RhCl(C_8H_{12})]_2$, $[Rh(C_8H_{12})dppp]BF_4$(dppp=$Ph_2PCH_2CH_2CH_2PPh_2$), $[Rh(C_8H_{12})dppp]PF_6$, $[Rh(C_8H_{12})dppp]OTf$(OTf=$SO_3CF_3$), $[Rh(C_8H_{12})dppp]ClO_4$, $[IrCl(C_8H_{12})]_2$, $IrCl(CO)(PPh_3)_2$, $IrH(CO)(PPh_3)_3$, $NiCl_2dppe$(dppe=$Ph_2PCH_2CH_2PPh_2$), $Pd(PPh_3)_4$, $PdCl_2(PPh_3)_2$, $Pt(PPh_3)_4$, $Pt(PhCH=CHCOCH=CHPh)_2$, $PtCl_2(P-n-Bu_3)_2$, $RuH_2(CO)(PPh_3)_3$, $RuHCl(PPh_3)_3$, $RuHCl(CO)(PPh_3)_3$, $RuCl_2(PPh_3)_3$, $Cp_2Ti(CO)_2$(Cp=$C_5H_5$) $Cp_2TiMe_2$, $Cp_2ZrClH$, $Sm(C_5Me_5)_2(thf)$, $SmI_3$, and the like are included.

It is preferable that a reaction between a borazine compound and an alkene compound is carried out in the presence of a compound which becomes a ligand of a metal complex. The yield of hexaalkylborazine produced can be improved by proceeding a reaction with adding the compound which becomes a ligand of a metal complex, into a reaction system.

The reason for the yield improvement is not clear, however, it is estimated that insertion and elimination rates of an alkene compound at the metal are controlled by change in a ligand coordinating to a metal, which may contribute to reaction yield improvement. As the other reason, the complex may be deactivated by the trace addition of certain impurity to the complex; however, by the addition of a compound which becomes a ligand of a metal complex, a reaction between the complex and the impurity can be suppressed, resulting in prevention of deactivation of the complex. However, it is only a speculation of the mechanism and even in a case wherein yield is improved by other factor, which is included to the scope of the present invention.

As a compound which becomes a ligand of a metal complex, such as a phosphorous ligand, a nitrogen ligand, a carbon ligand and an oxygen ligand can beused and includes specifically tripherlylphosphine ($PPh_3$), bis(diphenylphosphino)methane ($Ph_2PCH_2PPh_2$), 1,2-bis(diphenylphosphino)ethane ($Ph_2PCH_2CH_2PPh_2$), 1,3-bis(diphenylphosphino)propane ($Ph_2PCH_2CH_2CH_2PPh_2$), 1,4-bis(diphenylphosphino)butane ($Ph_2PCH_2CH_2CH_2CH_2PPh_2$), $PMe_2Ph$, $P(OMe)_2Ph$, $P(OMe)Ph_2$, $P(OMe)_3$, $Pet_2PH$, $P(OEt)_2PH$, $P(OEt)PH_2$, $P(OEt)_3$, $Me_2PCH_2CH_2CH_2PMe_2$, 2,2'-bipyridine, 1,5-cyclooctadiene, norbornadiene, cyclopentadienyl ligand ($C_5H_5$), carbon monoxide and tetrahydrofuran.

Conditions of a reaction between a borazine compound and an alkene compound are not especially limited. A solution containing a borazine compound may be used. A reaction type is influenced by reaction temperature and reaction pressure. A borazine compound and a catalyst may be included in a solvent.

A solvent used is not especially limited, and includes aromatic compounds such as toluene and xylene. In a reaction of a borazine compound represented by the chemical formula 1, by using an aromatic compound as a solvent, reaction heat can be efficiently removed. A reaction between a borazine compound and an alkene compound may be carried out without using a solvent. When a reaction is carried out without using a solvent, reduction of raw material cost and simplification of reaction equipment can be attained.

Pressure and temperature conditions are preferably controlled in response to types of a borazine compound and an alkene compound used. A borazine compound represented by the chemical formula 1 has such structure that an alkyl group is bonded to each nitrogen atom, which may provide large steric hindrance against a reaction with an alkene compound. In consideration of this estimation, a reaction is preferably carried out under high pressure and/or high temperature condition.

Reaction temperature is preferably −196 to 200° C., more preferably −78 to 100° C., further preferably −20 to 100° C. and particularly preferably 0 to 90° C. By carrying out a reaction within this temperature range, a reaction can be carried out efficiently, even if reaction suppression reasons such as steric hindrance are present. Reaction temperature can be measured by a temperature sensor such as a K thermocouple.

Use amount of an alkene compound based on a borazine compound may be determined in consideration of structure of a borazine compound. For example, when all of $R^1$s are hydrogen atoms, it is preferable that an alkene compound of at least three times of a borazine compound is contacted with a borazine compound. When one of $R^1$s is a hydrogen atom, an alkene compound of the same quantity of a borazine compound may be used. For a borazine compound in liquid state, when such an aspect is used that an alkene compound is fed and reacted in gaseous state, a reaction is preferably carried out by feeding excess alkene compound to peripheral of liquid containing a borazine compound.

Use amount of a catalyst depends on a catalyst type, however, in general, 0.0001 to 0.1 mole of a catalyst is used based on 1 mole of a borazine compound used. By using a catalyst within this range, the reaction is promoted effectively.

Use amount of a solvent to carry out a reaction using a solvent is also not especially limited, however, too small amount may result in ineffective removal of reaction heat by a solvent. Too much amount of a solvent may also raise a problem of increasing production cost or an added process required to remove a solvent after a reaction. In view of these in consideration, solvent amount is preferably 0.1 to 100 times of a borazine compound.

When a compound which becomes a ligand of a metal complex is added, the addition amount depends on the type and is not especially limited. Generally, a compound which becomes a ligand of a metal complex is preferably 0.5 to 3.0 mole equivalent to 1 mole of a metal complex.

An alkyl borazine compound produced is hexaalkylborazine having structure represented by the chemical formula 2. In the present invention, "an alkylborazine compound" means hexaalkylborazine represented by the chemical formula 2, unless otherwise specified.

[Chemical formula 2]

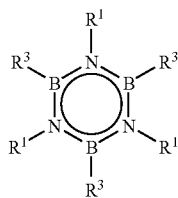

wherein each $R^1$ is an alkyl group; $R^1$s in the alkylborazine compound may be the same or different; and each $R^1$ is a group derived from $R^1$ in the chemical formula 1. Explanation on $R^1$ is omitted here because it is as explained in $R^1$ of the chemical formula 1.

Each $R^3$ is an alkyl group derived from an alkene compound. When an alkene compound is represented by $R^4$—HC=CH$_2$, $R^3$ is derived from —CH$_2$—CH—$R^4$.

$R^3$s may be the same or different. In consideration of yield of a synthesis reaction or handling easiness, $R^3$s are preferably the same alkyl groups. The alkyl group may be any of straight chain, branched or cyclic type. The number of carbon atoms of the alkyl group are not especially limited, however, preferably 2 to 8 and more preferably 2 to 4. Specific examples of the alkyl group include such as ethyl group, propyl group, isopropyl group, butyl group, isobutyl group, sec-butyl group, tert-butyl group, pentyl group, isopentyl group, neopentyl group, hexyl group, heptyl group, octyl group, nonyl group, decyl group, cyclopropyl group, cyclopentyl group and cyclohexyl group. Alkyl groups other than these may also be used.

Specific alkylborazine compounds include such as hexaethylborazine, hexa(n-propyl)borazine, hexa(iso-propyl)borazine, hexa(n-butyl)borazine, hexa(sec-butyl)borazine, hexa(iso-butyl)borazine, hexa(tert-butyl)borazine, hexa(1-methylbutyl)borazine, hexa(2-methylbutyl)borazine, hexa(neo-pentyl)borazine, hexa(1,2-dimethylpropyl)borazine, hexa(1-ethylpropyl)borazine, hexa(n-hexyl)borazine, hexacyclohexylborazine, B,B',B"-triethyl-N,N',N"-trimethylborazine, B,B',B"-triethyl-N,N',N"-tri(n-propyl)borazine, B,B',B"-triethyl-N,N',N"-tri(iso-propyl)borazine, B,B',B"-tri(iso-propyl)-N,N',N"-trimethylborazine and B,B',B"-tri(iso-propyl)-N,N',N"-triethylborazine.

It is preferable that an alkylborazine compound synthesized is purified. A method for purification may be selected, as appropriate, from a known purification method such as distillation purification and sublimation purification.

Technique of distillation purification is not especially limited, as long as it can separate an objective alkylborazine compound and impurities. Before distillation purification, general treatment in the field of organic synthesis may be performed. For example, a reaction solution may be filtered and concentrated using an evaporator.

Scale and type of distillation purification equipment may be determined in response to environment or scale to which the present invention is applied. For example, to treat a large quantity of a crude product, an industrial scale distillation tower may be used. While, to treat a small quantity of a crude product, distillation purification using a distillation tube can be used. For example, as a specific example of equipment for distillation purification to treat a small quantity of a crude product, distillation equipment attached with a Liebig cooling tube by a Claisen type connecting tube to a 3-neck flask may be used. However, the scope of the present invention is by no means limited to the embodiments using these equipment for distillation purification.

Sublimation purification is a purification method to separate impurities and an objective substance by utilization of difference in sublimation temperature of compounds. Embodiments of sublimation purification are not especially limited and morphology of sublimation purification equipment may be selected, as appropriate, in response to production scale or production environment of an alkylborazine compound. By strict temperature control by gas flow, purity of an objective substance obtained can be improved.

In the production method according to the present invention, borazine is substituted with an alkyl group without using a Grignard reagent, and therefore generation of trialkylborane is suppressed. The reaction can also be carried out without using ether usually used in a Grignard reaction. Comparing with a Grignard reagent, an alkene compound is generally cheaper and thus production cost of an alkylborazine compound can be reduced. Also by comparing with a production of an alkylborazine compound using a Grignard reaction, reaction time can be shortened. Thus, the production method according to the present invention has various advantageous effects in producing an alkylborazine compound in industrial scale.

An alkylborazine compound produced can be used, but not limited, to form, for example, an interlayer dielectric film for semiconductor, a barrier metal layer and an etching stopper layer. In this case, an alkylborazine compound or a modified form of an alkylborazine compound may be used. A polymer obtained by polymerization of an alkylborazine compound or an alkylborazine compound derivative may be used as raw material of an interlayer dielectric film for semiconductor, a barrier metal layer and an etching stopper layer.

A polymer may be formed by using a compound having borazine-ring backbone as a monomer. Polymerization method or polymerization morphology is not especially limited. A polymerization method may be selected based on a functional group bonded to a borazine ring. For example, when an amino group is bonded, a polymer may be synthesized by polycondensation. When a vinyl group or a vinyl-containing functional group is bonded to a borazine ring, a polymer may be formed by radical polymerization using a polymerization initiator. A polymer may be a homopolymer or a copolymer containing 2 or more monomer units. Copolymer morphology may be any of a random copolymer, a block copolymer or a graft copolymer. By using a monomer having 3 or more functional groups formable a bond with other monomer, a network-likely bonded polymer can be obtained.

Then a method for forming an interlayer dielectric film for semiconductor, a barrier metal layer or an etching stopper layer is explained. In the following explanation, "an alkylborazine compound", "derivatives of an alkylborazine compound" and "a polymer induced from these" are named totally as "a borazine-ring containing compound".

To form an interlayer dielectric film for semiconductor, a barrier metal layer or an etching stopper layer using a borazine-ring containing compound, a solution or slurry like composition containing a borazine-ring containing compound is first prepared and this composition is coated to form a coated film. A solvent used here to dissolve or disperse a borazine-ring containing compound is not especially limited, as long as it can dissolve or disperse a borazine-ring containing compound or other components added, if necessary. As a solvent here, for example, alcohols such as ethylene glycol, ethylene glycol monomethyl ether, etc.; aromatic hydrocarbons such as toluene, benzene, xylene, etc.; hydrocarbons such as hexane, heptane, octane, etc.; tetrahydrofuran, diglyme, tetraglyme, and the like can be used. They may be used as a single component or in combination of two or more types. Diglyme is preferable for film formation using spin coating. When diglyme or derivatives thereof is used, uniformity of a film produced is improved and also white turbidity of a film can be prevented. Use amount of a solvent to dissolve or disperse a borazine-ring containing compound should not especially be limited, and may be determined in response to production means of low dielectric material. For example, for film formation using spin coating, a solvent type and use amount of the solvent may be determined so that viscosity suitable to spin coating is obtained.

A composition containing a borazine-ring containing compound is fed to a place desired, and solidified by drying. For example, to form an interlayer dielectric film for semiconductor, it is coated on a substrate by spin coating and dried. When a coated film with desired thickness can not be obtained by one coating and drying step, coating and drying may be repeated until desired thickness is attained. Film formation conditions such as rotation number of a spin coater, temperature for drying and time for drying are not especially limited.

Coating on a substrate may also be performed using a method other than spin coating. For example, spray coating, dip coating, and the like may be used.

Then a coated film is dried. Drying temperature of a coated film is usually from 100 to 250° C. Drying temperature here means maximum temperature in drying treatment. For example, when drying temperature is gradually increased and held at 100° C. for 30 minutes, followed by cooling, "drying temperature" is defined to be 100° C. Drying temperature can be measured by a thermocouple. Drying time for a coated film is not especially limited. It may be determined, as appropriate, considering characteristics of low dielectric material obtained, such as dielectric constant, humidity resistance, and the like.

EXAMPLES

Example 1

Into a flask equipped with a stirrer and a cooling tube, after purging with nitrogen, 26.8 g of methylammonium chloride, 16.8 g of sodium borohydride and 395 g of triglyme were charged and temperature was raised to 180° C. over 2 hours. After maintaining at 180° C. for 3 hours, liquid was removed into a receiving vessel placed at the forefront of the cooling tube. This liquid was transferred to a different flask equipped with a cooling tube, and subjected to distillation purification to obtain 12.8 g of transparent N-trimethylborazine.

Into an autoclave, 12.2 g of purified N,N',N"-trimethylborazine (TMB), 250 g of toluene, as a solvent, and 1.0 g of hydridocarbonyl tris(triphenylphosphine)rhodium(I) (RhH(CO)(PPh$_3$)$_3$), as a catalyst, were charged. Further, as an alkene compound, ethylene was introduced so that pressure was 8.5 kg/cm$^2$ at 25° C. and reaction was carried out for 10 hours by standing still.

After removing toluene from the reaction solution, distillation purification was carried out to obtain 4.1 g of B,B',B"-triethyl-N,N',N"-trimethylborazine (TETMB) (yield of 20%). GC-MS measurement was carried out on TETMB obtained to confirm presence or absence of trialkylborane. As a result, trialkylborane was not detected. The results are shown in Table 1.

Comparative Example 1

Into a 500 mL five necked flask were charged, in nitrogen atmosphere, 20.6 g of B,B',B"-trichloro-N,N',N"-trimethylborazine (TCTMB) and 40 mL of diethyl ether as a solvent. By controlling inner temperature of the reaction system within 20° C.±5° C., a diethyl ether solution (3M, 100 mL) of ethylmagnesium bromide (EMB), as a Grignard reagent, was added drop-wise over 2 hours. Subsequently, by refluxing for 2 hours and maturing, a synthesis reaction of B,B',B"-triethyl-N,N',N"-trimethylborazine (TETMB) was progressed. After temperature of the reaction solution was lowered to room temperature, the reaction solution was filtered and concentrated by removing only ether from the filtrate using an evaporator. Thus concentrated solution was stood still to precipitate a solid substance and supernatant was drawn out (yield of 14.2 g).

Drawn out supernatant was charged into a 3 necked 100 mL flask, and subjected to distillation under reduced pressure to obtain TETMB. GC-MS measurement was carried out on TETMB obtained to confirm presence or absence of trialkylborane. As a result, 1% by weight of triethylborane was detected. The results are shown in Table 1.

TABLE 1

|  | Raw materials | | Content of trialkylborane |
|---|---|---|---|
| Example 1 | TMB | ethylene | None |
| Comparative Example 1 | TCTMB | EMB | 1% |

TMB: N,N',N"-trimethylborazine
TCTMB: B,B',B"-trichloro-N,N',N"-trimethylborazine
EMB: ethylmagnesium bromide Example 2

Into an autoclave, 12.2 g of TMB, 250 g of toluene as a solvent, 0.43 g of 1,2-bis(diphenylphosphino)propane as a ligand compound of a metal complex and 1.0 g of hydridocarbonyl tris(triphenylphosphine)rhodium(I) (RhH(CO)(PPh$_3$)$_3$) as a catalyst were charged. Further, as an alkene compound, ethylene was introduced so that pressure was 8.5 kg/cm$^2$ at 25° C. and a reaction was progressed for 10 hours by standing still. After removing toluene from the reaction solution, distillation purification was carried out to obtain 16.5 g of TETMB (yield of 80%).

Evaluation

As shown by Example 1 and Comparative Example 1 in Table 1, by adopting a method for a reaction between a borazine compound and an alkene compound, generation of trialkylborane can be suppressed.

Also by comparing Example 1 and Example 2, the addition of a compound, which becomes a ligand of a metal complex, was found to significantly improve yield.

What is claimed is:

1. A method for producing hexaalkylborazine, wherein hexaalkylborazine represented by the chemical formula 2 is synthesized by a reaction of a borazine compound represented by the chemical formula 1 with an alkene compound, in the presence of a catalyst:

[Chemical formula 1]

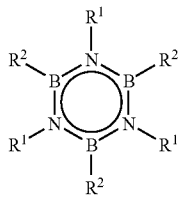

wherein $R^1$s may be the same or different and each $R^1$ represents an alkyl group;

and each $R^2$ represents a hydrogen atom or an alkyl group, and at least one of $R^2$s represents a hydrogen atom:

[Chemical formula 2]

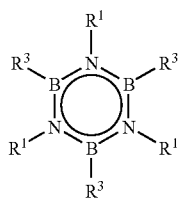

wherein $R^1$s and $R^3$s may be the same or different and each $R^1$ and $R^3$ represents an alkyl group.

2. A method for production according to claim 1, wherein the catalyst is a metal catalyst.

3. A method for production according to claim 2, wherein the reaction is carried out in the presence of a compound which becomes a ligand forming a metal complex by coordinating the metal catalyst.

4. A method according to claim 3, wherein the ligand is a phosphorus ligand, a nitrogen ligand, a carbon ligand, or an oxygen ligand.

5. A method according to claim 3, wherein the ligand is PPh$_3$, Ph$_2$PCH$_2$PPh$_2$, Ph$_2$PCH$_2$CH$_2$PPh$_2$, Ph$_2$PCH$_2$CH$_2$CH$_2$PPh$_2$, Ph$_2$PCH$_2$CH$_2$CH$_2$CH$_2$PPh$_2$, PMe$_2$Ph, P(OMe)$_2$Ph, P(OMe)Ph$_2$, P(OMe)$_3$, PEt$_2$Ph, P(OEt)$_2$Ph, P(OEt)Ph$_2$, P(OEt)$_3$, Me$_2$PCH$_2$CH$_2$CH$_2$PMe$_2$, 2,2'-bipyridine, 1,5-cyclooctadiene, norbornadiene, cyclopentadienyl ligand, carbon monoxide and tetrahydrofuran.

6. A method according to claim 3, wherein the ligand is used in an amount of 0.5 to 3.0 moles per mole of the catalyst.

7. A method for producing hexaalkylborazine, comprising synthesizing hexaalkylborazine represented by the chemical formula 2 by a reaction of a borazine compound represented by the chemical formula 1 with an alkene compound, in the presence of a catalyst:

[Chemical formula 1]

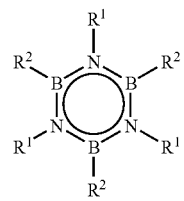

wherein $R^1$s may be the same or different and each $R^1$ represents an alkyl group;

and each $R^2$ represents a hydrogen atom or an alkyl group, and at least one of $R^2$s represents a hydrogen atom:

[Chemical formula 2]

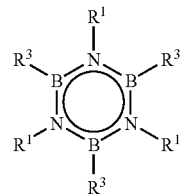

wherein $R^1$s and $R^3$s may be the same or different and each $R^1$ and $R^3$ represents an alkyl group.

* * * * *